US006475546B1

(12) United States Patent
Harz et al.

(10) Patent No.: US 6,475,546 B1
(45) Date of Patent: Nov. 5, 2002

(54) PROCESS FOR PRODUCING ENZYME-CONTAINING GRANULES

(75) Inventors: Hans-Peter Harz, Dudenhofen; Wolfgang Heinzl, Wachenheim; Franz-Josef Schöner, Edenkoben; Roland Betz, Niederkirchen; Thomas Kessler, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/868,725

(22) PCT Filed: Dec. 18, 1999

(86) PCT No.: PCT/EP99/10139

§ 371 (c)(1),
(2), (4) Date: Jun. 21, 2001

(87) PCT Pub. No.: WO00/36927

PCT Pub. Date: Jun. 29, 2000

(30) Foreign Application Priority Data

Dec. 22, 1998 (DE) .......................................... 198 59 385

(51) Int. Cl.⁷ .............................. A23P 1/12; B29B 9/06; A23K 1/165
(52) U.S. Cl. ..................................................... 426/516
(58) Field of Search ............................. 426/61, 52, 516, 426/519; 366/38, 133, 134, 156.2; 264/211, 142, 143, 211.11, 211.15, 211.21; 425/130, 131.1, 209

(56) References Cited

U.S. PATENT DOCUMENTS

| 4,009,076 A | * | 2/1977 | Green et al. ................. 427/154 |
| 4,087,368 A | * | 5/1978 | Borrello ..................... 435/187 |
| 4,286,058 A | * | 8/1981 | Wenger et al. ................. 127/38 |
| 4,408,725 A | * | 10/1983 | Wenger et al. ........... 241/260.1 |
| 5,290,496 A | * | 3/1994 | Carduck et al. ............. 264/142 |
| 5,507,840 A | | 4/1996 | Schrell .......................... 8/532 |
| 5,575,821 A | | 11/1996 | Schrell .......................... 8/493 |

FOREIGN PATENT DOCUMENTS

| EP | 257 996 | 3/1988 |
| EP | 564 476 | 10/1993 |
| WO | 97/12958 | 4/1997 |
| WO | 98/54980 | 12/1998 |

OTHER PUBLICATIONS

Reigh et al., "Enzyme treatment of catfish feeds . . .", Louisiana Agriculture, vol. 44, No. 3, Summer 2001.*
Harper et al., "Feeding phytase to growing pigs . . .", Livestock Update, Feb. 1999, Virginia Cooperative Extension.*
Pereira et al., "Enzymatic extrusion of potato starch using alpha–amylase with different plasticizer ratios (water:glycerol)", http://www.confex.com/ift/98annual/accepted/642.htm; Jan. 1998.*
Patent Abst.of Japan, No. 62294039, Dec. 1987.

* cited by examiner

*Primary Examiner*—Keith Hendricks
(74) *Attorney, Agent, or Firm*—Keil & Weinkauf

(57) ABSTRACT

The invention relates to a method for producing granulates which contain enzymes and which are suited for feeding animals. The granulates are produced by mixing at least one enzyme with a supporting material and by extruding this mixture. The inventive method is characterized in that the supporting material is firstly plasticized in a screw mixer which is equipped with at least one horizontally arranged screw. Afterwards, the enzyme is introduced into the screw mixer and is processed with the plasticized supporting material to produce a homogeneous material which is then extruded.

8 Claims, No Drawings

PROCESS FOR PRODUCING ENZYME-CONTAINING GRANULES

This application is a 371 of PCT/EP99/10139, filed Dec. 18, 1999.

The present invention relates to a novel process for producing enzyme-containing granules suitable for animal nutrition, by mixing at least one enzyme with a carrier material and extruding this mixture.

The use of enzyme-containing materials in animal nutrition is generally known. Such compositions promote digestion and thus improve feed utilization and energy intake from the feed.

EP-B 257 996 describes enzyme-containing premixes for animal nutrition which are obtained by absorbing aqueous enzyme solutions onto a cereal-based carrier with subsequent pelleting of the carrier-enzyme complex.

WO 97/12958 discloses the production of enzyme-containing microgranules by fluidized-bed granulation, a premix of an aqueous enzyme solution and a binder being applied to a carrier in the fluidized bed and the resultant material then being provided with a coating of a water-soluble polymer.

EP-B 564 476 describes a process for producing enzyme granules by extruding a free-flowing enzyme premix produced by mixing a fermentation broth with additives.

However, the known processes are relatively complex and the resultant products still leave room for improvement with respect to product stability and particle size distribution.

It is an object of the present invention to find a process for producing enzyme-containing granules for use in animal nutrition, which process leads to improved product properties.

We have found that this object is achieved, accordingly, by a process for producing enzyme granules, which are suitable for animal nutrition, by mixing at least one enzyme with a carrier material and extruding this mixture, which comprises first plasticizing the carrier material in a screw extruder equipped with at least one horizontal screw, then introducing the enzyme into the screw extruder and processing it together with the plasticized carrier material to form a homogeneous mixture and extruding this.

The inventive process is suitable in principle for processing all enzymes or enzyme mixtures, in particular those which are suitable for animal nutrition. Enzymes which come into consideration are, for example:

oxidoreductases, transferases, lyases, isomerases or ligases, and in particular hydrolases. Hydrolases, that is to say enzymes which can cause hydrolytic cleavage of bonds, are, for example, esterases, glycosidases, etherhydrolases, proteases, amidases, aminidases, nitrilases or phosphatases. The glycosidases include, for example, both endo- and exo-glucosidases which can cleave both α- and β-glycosidic bonds, for example amylase, maltase, cellulase, endoxylanase, β-glucanase, mannanase, or lysozyme, and in addition galactosidase or β-glucuronidases. Preferably, non-starch-polysaccharide-cleaving enzymes are processed. Very particular preference is given to phytase.

The enzymes are generally used as aqueous solutions, preferably as aqueous retentates of an ultrafiltration, as obtained in a manner known per se from fermentation processes.

The dry mass of enzyme is in the range from 15 to 35, preferably from 20 to 25% by weight, at 10,000 to 35,000 IU/g. The aqueous enzyme solutions are used in amounts such that from 1000 to 8000 units/g are present in the granules.

However, the enzymes can also be used in the appropriate amounts in the form of dry powders.

Particularly preferably, phytase ultrafiltrates are used according to the invention.

Suitable aids for the carrier matrix are in principle all aids suitable for animal nutrition which sufficiently rapidly release the enzymes under the pH conditions in the alimentary tract of the animals and have good compatibility with the enzymes. Suitable aids are, for example, polymeric binders such as polyvinylpyrrolidone, copolymers of N-vinylpyrrolidone and N-vinylacetate, for example a VP-VAc copolymer 6+4, or cellulose derivatives such as hydroxypropyl cellulose or preferably hydroxypropyl methyl cellulose, and in addition polyvinyl acetate, polyvinyl alcohol, polyacrylates or polymethacrylates. Also suitable are cereal products, for example wheat middlings bran, or milk products, for example skimmed milk powder. Suitable carrier materials are also, in particular, fats and waxes.

Also suitable are all types of starches, in addition oligosaccharides such as dextrins, and di- and monosaccharides, for example, sucrose, lactose, fructose, galactose, mannose or sorbose. Carrier matrix materials which come into consideration are, in addition, low-molecular-weight polyethylene glycols having molecular weights of from 200 to 20,000 g/mol, preferably from 5000 to 8000 g/mol. Also suitable are polyoxyethylene-polyoxypropylene block copolymers, which are also known as poloxamers.

Particularly preferably, the carrier materials used are mixtures of starch and polyethylene glycols.

In addition, gelatin or other proteins can also be added to the carrier materials in amounts of up to 50% by weight. In addition, the carrier materials can comprise inorganic additives, such as lime, bentonites or silicates.

The proportion of the carrier materials of the total weight of the granules is, based on the granulate dry weight, up to 99.9% by weight, preferably from 50 to 99% by weight, particularly preferably from 88 to 98% by weight.

In addition, minerals, for example magnesium sulfate, zinc sulfate or sodium sulfate, can also be added to the carrier materials. Furthermore, to set the pHs, the addition of further salts, for example acetates, tartrates or citrates, can also be helpful.

According to the invention all components for the carrier material can be added to a premix and introduced into the screw extruder or else individual aid components can be added at a later time point during extrusion.

To mix and homogenize the carrier materials and the enzyme-containing ultrafiltrate or the dry enzyme powder, all screw extruders having at least one horizontal screw are suitable. The inventive process also permits, in addition to the use of single-screw extruders, the use of meshing or non-meshing multiple-screw extruders, in particular twin-screw extruders which can be corotating or counterrotating.

According to the invention, the components of the carrier matrix are first plasticized in a screw extruder by supplying mechanical and thermal energy. Depending on the type of carrier materials this can be achieved, for example, by melting the components. Plasticization can be carried out at temperatures in the range from 20 to 250° C.

After the carrier materials or their mixtures have been sufficiently plasticized and homogenized, the mixture is cooled and then the ultrafiltrate or the dry enzyme powder is introduced into the screw extruder. Introduction can be carried out, for example, in a manner such that the aqueous ultrafiltrate or the dry enzyme powder is fed to the screw barrel via suitable metering apparatuses. The mixture temperature of the carrier materials at this point is preferably no higher than 70° C., particularly preferably from 20 to 60° C. The length of the screw channel is preferably chosen so that the total residence time of the mixture in the extruder is less than 10 min., preferably less than 2 min. In particular in extruder sections in which the mixture temperature is greater than 30° C., the residence time should be less than 2 min. After the homogenization, generally discharge from the extruder and shaping take place. In this case the homogenized mixture can be extruded via a die or through a pelletizing die. The exiting strands can be shaped to form uniform granules by hot-cut or cold-cut pelletizing.

The mixture can also be partially dried in the extruder by applying a vacuum. Granules can also be discharged directly from the extruder, more precisely by equipping the screw with grinding elements at its end lying toward the extruder head. Extrusion is then performed via the open extruder head.

If desired, the resultant granules can then be subjected to an additional drying process.

The enzyme-containing granules obtained by the inventive process have mean particle sizes in the range from 500 to 2000 μm, preferably from 500 to 1000 μm.

They are suitable for use in feeds for poultry, pigs, calves or for use in aquaculture, for example in trout food or salmon food.

To produce the feed pellets, the enzyme granules are mixed with a foodstuff. Generally, for example, in the case of phytase-containing foodstuffs, contents of some ten to some hundred ppm of phytase are set. The feed is then pelleted, for which all commercially conventional types of pellet presses can be used. All of these pellet presses share the fact that the feed is first conditioned by steam introduction and is then pressed through the die. Depending on the die, pellets of a particle size from 2 to 12 mm can be produced in this manner. When the pellets are being pressed through the die, the maximum temperature loading of the pelleting process is reached. Temperatures of from 60 to 100° C. can be reached during this.

To evaluate the stability of the foodstuff enzymes during pelleting, a standard pelletization was established. To improve the analytical determination of content, the enzyme rate in the feed was increased. The pelleting process is carried out in such a manner that a pellet temperature of 80° C. is always achieved. In the pelleted feed, the enzyme activity is determined in comparison with the initial activity, with, if appropriate, a correction being made for the content of native enzyme. As a control, a standard is always carried through the pelleting process and analyzed.

Because of their favorable particle size distribution and the fact that the enzyme material is embedded in a stabilizing matrix, the granules have a high thermal stability, in particular during the processing to form feed pellets.

EXAMPLES

General Process Description

The granules are prepared in a double-screw extruder type ZSK 30, Werner & Pfleiderer. The extruder is operated with the following temperature profile:

Section 1: 40° C.; section 2: 100° C.; section 3: 120° C.; section 4: 60° C.;

section 5: 45° C.; section 6: 45° C.; section 7: 45° C.

The enzyme solution is added in section 6. The mixture is extruded through a pelletizing die and dried.

In this manner, formulations of the following composition may be processed:

| Formulation 1 | |
|---|---|
| Phytase | 4% by weight |
| Corn starch | 76% by weight |
| Polyethylene glycol 6000 | 20% by weight |

| Formulation 2 | |
|---|---|
| Phytase | 5% by weight |
| Corn starch | 88.6% by weight |
| Lutrol ® F127 (Poloxamer 407) | 2.4% by weight |
| MgSO$_4$ | 4% by weight |

| Formulation 3 | |
|---|---|
| Phytase | 6% by weight |
| Corn starch | 70% by weight |
| Lutrol ®F127 (Poloxamer 407) | 20% by weight |
| MgSO$_4$ | 4% by weight |

| Formulation 4 | |
|---|---|
| Phytase | 6% by weight |
| Corn starch | 76% by weight |
| Hydroxypropyl methyl cellulose | 15% by weight |
| MgSO$_4$ | 3% by weight |

| Formulation 5 | |
|---|---|
| Phytase | 5% by weight |
| Corn starch | 90% by weight |
| Fat | 5% by weight |

| Formulation 6 | |
|---|---|
| Phytase | 7% by weight |
| Corn starch | 68% by weight |
| Lutrol ® F68 (Poloxamer 188) | 25% by weight |

| Formulation 7 | |
|---|---|
| Phytase | 8% by weight |
| Corn starch | 75% by weight |
| Hydroxypropyl methyl cellulose | 7.5% by weight |
| Copovidone | 7.5% by weight |
| MgSO$_4$ | 2% by weight |

| Formulation 8 | |
|---|---|
| Phytase | 10% by weight |
| Corn starch | 83% by weight |
| Hydroxypropyl methyl cellulose | 2.5% by weight |
| Copovidone | 2.5% by weight |
| MgSO$_4$ | 2% by weight |

| Formulation 9 | |
|---|---|
| Phytase | 6.5% by weight |
| Corn starch | 90% by weight |
| Polyvinyl alcohol | 3.5% by weight |

Pelleting experiment

The granules are processed together with a foodstuff (see the table below for the composition) in a pelleting machine from CPM (California Pellet Mill Company) to form pellets at temperatures in the range from 70 to 80° C. The enzyme retention (in each case corrected for native phytase) is determined as described in "Bestimmung der Phytaseaktivität in Futtermitteln und Vormischungen" [Determination of phytase activity in feedstuffs and premixes], VDLUFA-Methodenbuch [VDLUFA Methods Handbook], Volume III, 4$^{th}$ supplement, 1997.

TABLE

| Composition of pig finishing feed | |
|---|---|
| Components | % by weight |
| Corn | 20.70 |
| Barley | 40.00 |
| Tapioca | 10.00 |
| Oats | 10.00 |
| Soyabean meal | 13.00 |
| Fish meal | 3.00 |
| Wheat bran | 0.84 |
| Soyabean oil | 0.50 |
| Agricultural lime | 1.20 |
| Cattle salt | 0.20 |
| Trace elements | 0.06 |
| DL-methionine | 0.05 |
| Choline chloride (50%) | 0.05 |
| Propionic acid | 0.40 |

We claim:

1. A process for producing enzyme-containing granules suitable for animal nutrition, by mixing at least one enzyme with a carrier material and extruding this mixture, which comprises the steps of:
   a) first plasticizing the carrier material in a screw extruder equipped with at least one horizontal screw, and
   b) subsequently introducing the enzyme into the screw extruder and processing it together with the plasticized carrier material to form a homogeneous mixture, and extruding said mixture.

2. A process as claimed in claim 1, wherein the enzyme is added in the form of an aqueous solution.

3. A process as claimed claim 1, wherein the carrier material is a mixture of starch and at least one further thermoplastic polymer.

4. A process as claimed in claim 3, wherein mixtures of starch and polyethylene glycol are used.

5. A process as claimed in claim 3, wherein mixtures of starch and hydroxypropyl methyl cellulose are used.

6. A process as claimed in claim 1, wherein, before adding the enzyme, the temperature of the plasticized carrier material is at or below 70° C.

7. A process as claimed in claim 1, wherein the total residence time in the extruder screw barrel is <10 min.

8. A process as claimed in claim 1, wherein the enzyme is phytase.

* * * * *